US008650975B2

(12) United States Patent
Gerlach

(10) Patent No.: US 8,650,975 B2
(45) Date of Patent: Feb. 18, 2014

(54) TEST SPECIMEN FOR TESTING THROUGH-THICKNESS PROPERTIES

(75) Inventor: Robert Gerlach, Oxford (GB)

(73) Assignee: Rolls-Royce PLC, London (GB)

( * ) Notice: Subject to any disclaimer, the term of this patent is extended or adjusted under 35 U.S.C. 154(b) by 130 days.

(21) Appl. No.: 12/854,963

(22) Filed: Aug. 12, 2010

(65) Prior Publication Data

US 2011/0041627 A1  Feb. 24, 2011

(30) Foreign Application Priority Data

Aug. 18, 2009 (GB) .................................. 0914365.2

(51) Int. Cl.
*G01N 33/00* (2006.01)

(52) U.S. Cl.
USPC .......................................................... 73/866

(58) Field of Classification Search
USPC ........... 73/760, 788, 866, 794, 795, 796, 797, 73/798
See application file for complete search history.

(56) References Cited

U.S. PATENT DOCUMENTS

| 4,850,715 | A | * | 7/1989 | Gaffin | 374/52 |
| 4,895,027 | A | * | 1/1990 | Manahan, Sr. | 73/799 |
| 5,144,844 | A |   | 9/1992 | Mathiak et al. | |
| 2009/0007692 | A1 | * | 1/2009 | Ferguson et al. | 73/831 |

FOREIGN PATENT DOCUMENTS

| EP | 0 660 100 A2 | 6/1995 |
| EP | 1 742 033 A1 | 1/2007 |
| FR | 2 579 327 A1 | 9/1986 |
| JP | A-58-173450 | 10/1983 |
| SU | 1415124 A1 | 8/1988 |

OTHER PUBLICATIONS

British Search Report dated Nov. 13, 2009 in British Application No. GB0914365.2.
Smits et al.; "Design of a cruciform specimen for biaxial testing of fibre reinforced composite laminates;" *Composite Sciences and Technology*; 2000: pp. 964-975: vol. 66.
European Search Report dated Dec. 6. 2012 from European Patent Application No. 10 17 2598.

* cited by examiner

*Primary Examiner* — Daniel S Larkin
*Assistant Examiner* — Jamar Ray
(74) *Attorney, Agent, or Firm* — Oliff PLC

(57) ABSTRACT

The present invention relates to a test specimen for testing the through-thickness properties of a fiber-reinforced composite material. The specimen comprises a first loading portion having a first longitudinal axis in a first plane and a second loading portion having a second longitudinal axis in a second plane. The first and second planes are substantially parallel and the first and second axes are oblique. The first and second loading portions partially overlap to form a test gauge portion that is integral with the first and second loading portions. The first loading portion extends beyond the test gauge portion in opposite directions along the first axis and the second loading portion extends beyond the gauge portion in opposite directions along the second axis. This allows a force be applied to the test gauge portion through the first and second loading portions.

19 Claims, 7 Drawing Sheets

A-A

Fig.5
A 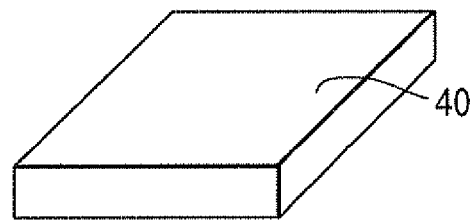
B 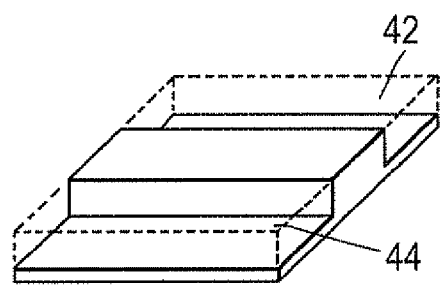
C 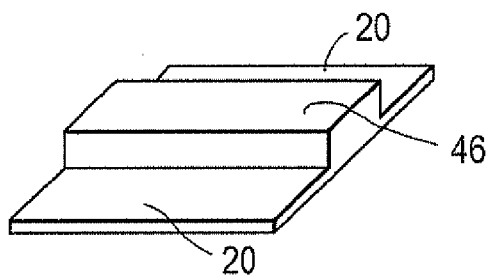
D 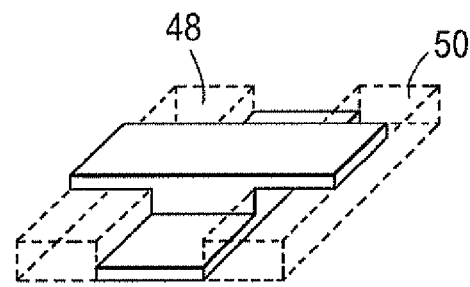
E 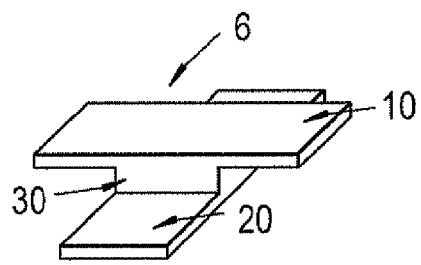

Fig.8
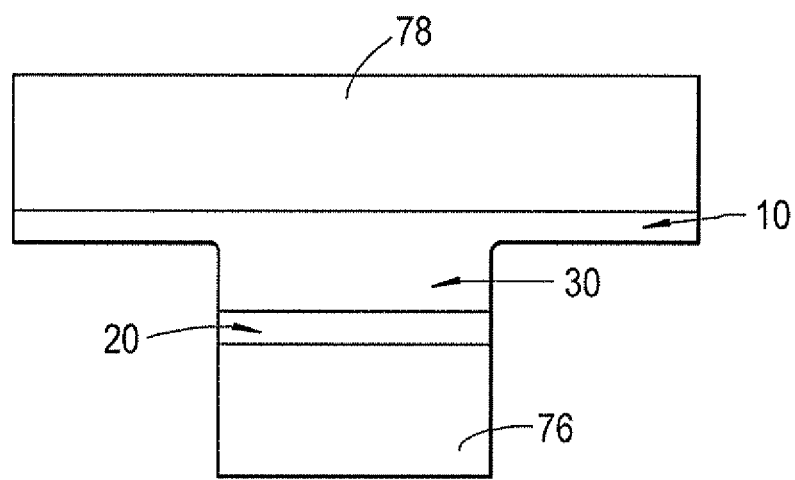
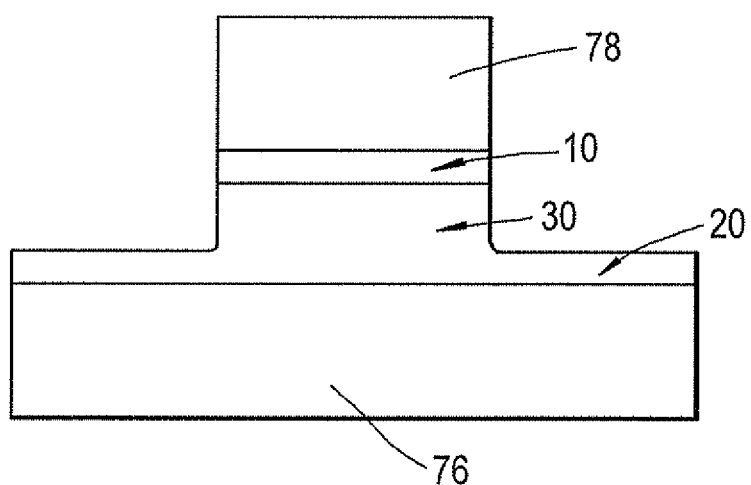

TEST SPECIMEN FOR TESTING THROUGH-THICKNESS PROPERTIES

The present invention relates to a test specimen, and a method of testing a specimen—in particular, a composite test specimen—and a method of manufacturing such a specimen.

Composite materials (otherwise known as 'composites') are materials that are made from two or more constituent materials. Fiber-Reinforced-Polymer (FRP) composites, comprising fibers embedded in a polymeric matrix system, are commonly used for many engineering applications. They can be classified into uni-directional (UD), two-dimensional (2D) and three-dimensional (3D) composites. Composites can offer certain advantages over conventional materials such as a high strength to weight ratio. However, physical properties of FRPs tend not to be isotropic. It is therefore necessary to be able to characterize the various physical properties of fiber-reinforced composites in a number of directions.

Testing the properties of fiber-reinforced composite plates in the through-thickness direction can be especially difficult. This is because composite plates are usually thin which means that it is difficult to transmit the load into the specimen. If the composite is reinforced in the through-thickness direction, as in the case of 3D composites, it becomes even more difficult to test the through-thickness properties because the composite is particularly strong in this direction, and the force needs to be transmitted in a way that allows the 3D reinforcement to maintain its reinforcing effect.

Figure 1:
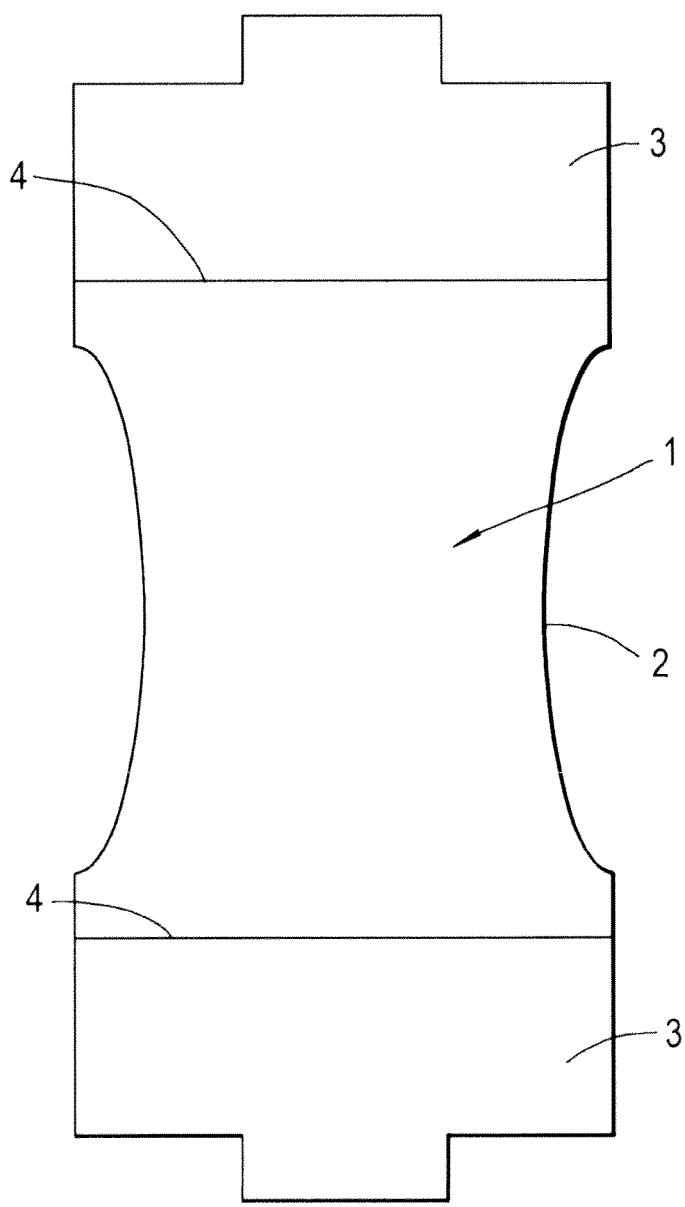

FIG. 1 shows a previously considered method of testing the tensile strength of UD and 2D FRP plates in the through-thickness direction. A test specimen 1 is provided that has a gauge section 2 having a reduced cross-sectional area. Metal end caps 3 are bonded to the ends of the specimen using an adhesive 4. A tensile force is then applied between the end caps 3 and this force is transmitted to the specimen through the adhesive bond 4. However, the adhesive bond 4 may be weaker then the composite. It is therefore necessary to produce a test specimen 1 that has a gauge section 2 having a cross-sectional area that is sufficiently smaller than the area of the adhesive bonds so as to ensure that the gauge section 2 fails in tension, not the adhesive bond 4.

However, it can be difficult to reduce sufficiently the cross-sectional area of the gauge section 2 because composite plates are usually relatively thin.

This becomes even more problematic if the composite plate is reinforced in the through-thickness direction because it is then even more difficult to produce an adhesive bond 4 of a sufficient strength such that in tension, the gauge section 2 always fails, and not the adhesive bond 4. Furthermore, force transmission into 3D reinforcing fiber tows oriented in the through-thickness direction using an adhesive bond is impractical, as the typical strength of the 3D reinforcement exceeds the strength of typically available adhesives by an order of magnitude.

Embodiments of the present invention aim to address at least some of the above problems.

According to the present invention there is provided a test specimen for testing the through-thickness properties of a fiber-reinforced composite material, a method of manufacturing such a specimen, and a method of testing such a specimen, as set out in the claims.

The invention may comprise any combination of the features and/or limitations referred to herein, except combinations of such features as are mutually exclusive.

Figure 2:
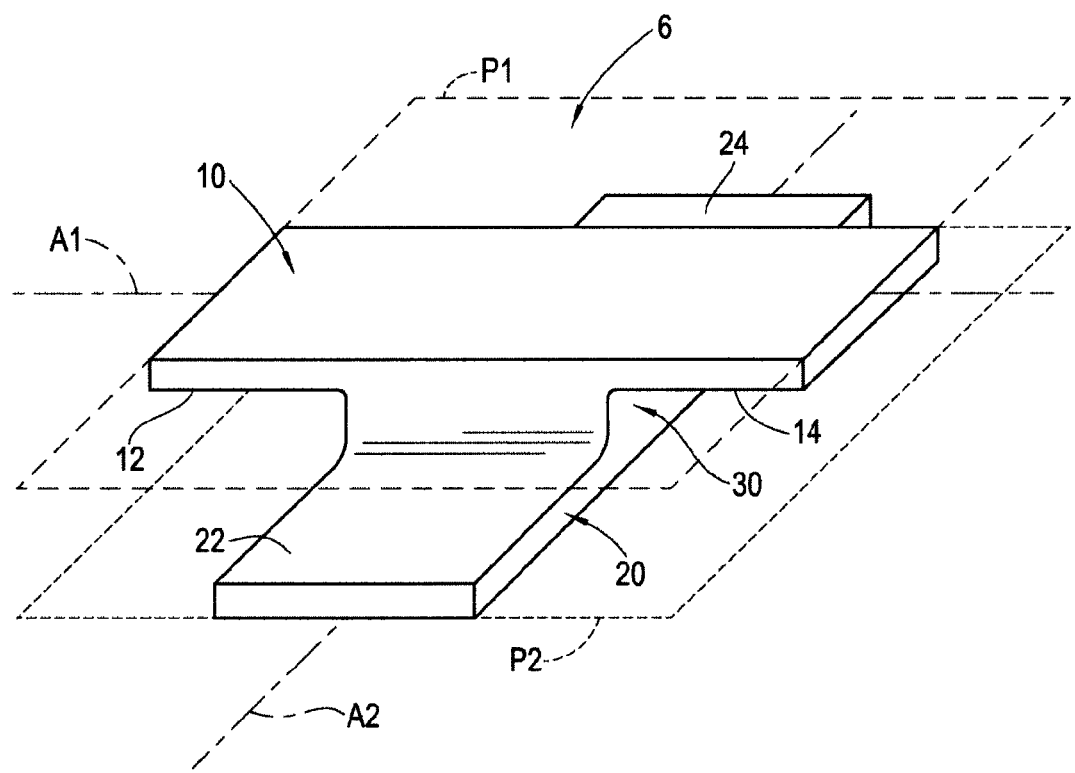
Figure 3A:
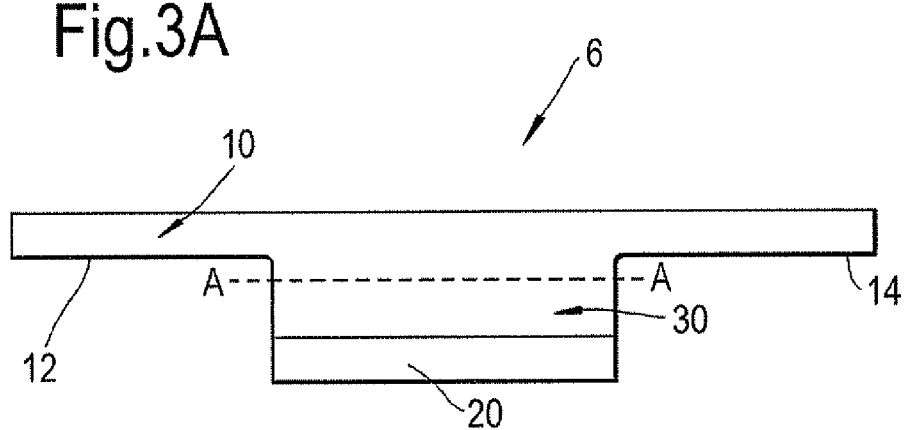
Figure 3B:
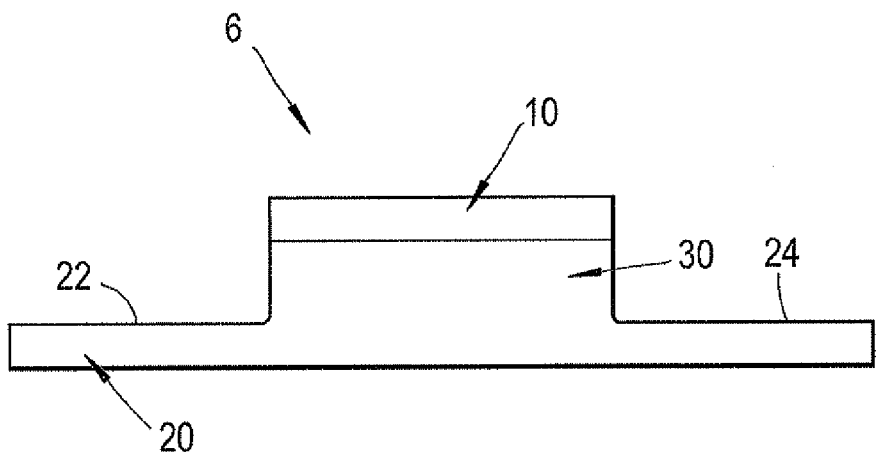
Figure 4:
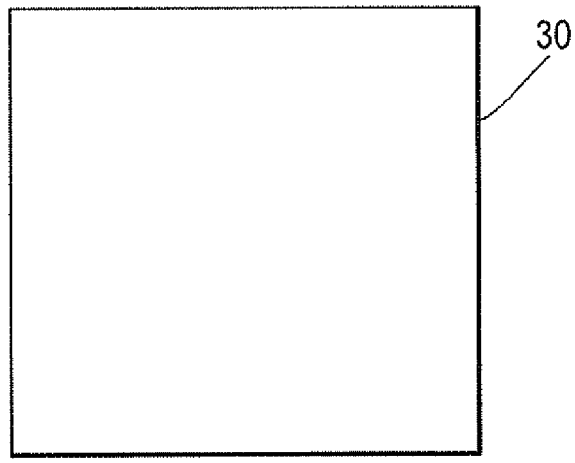
Figure 6:
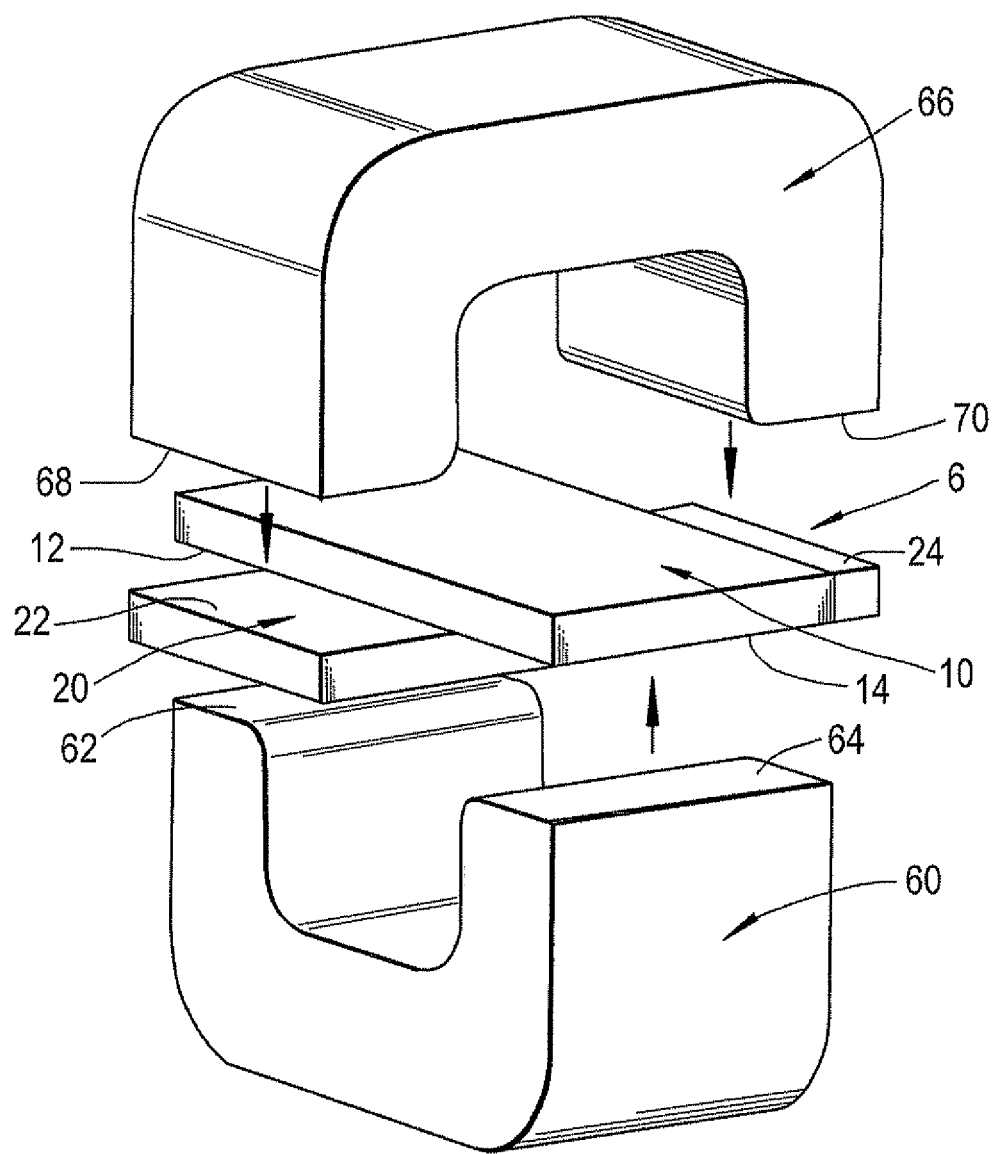
Figure 7:
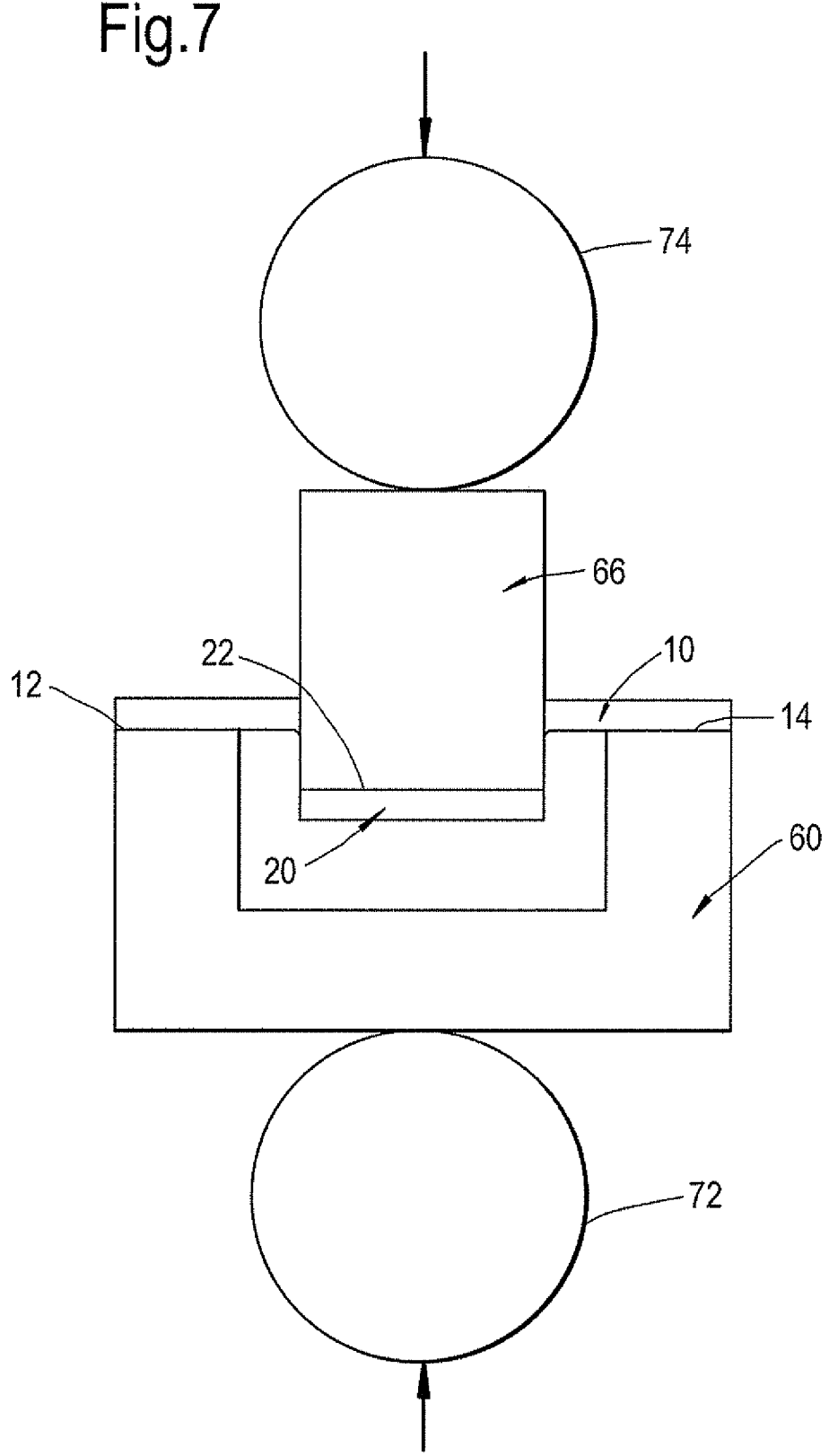

Embodiments of the present invention will now be described, by way of example, with reference to the accompanying drawings, in which:

FIG. 1 schematically shows a previously considered arrangement for testing a composite plate;

FIG. 2 schematically shows a perspective view of a test specimen according to the present invention;

FIGS. 3A and 3B schematically show a front and side view of the test specimen of FIG. 2;

FIG. 4 schematically shows the section A-A of FIG. 3;

FIGS. 5A-E schematically illustrate the steps of manufacturing a test specimen according to the present invention;

FIG. 6 schematically shows a test specimen in a test rig;

FIG. 7 schematically shows an experimental set-up for testing a test specimen according to the present invention; and FIG. 8 schematically shows a modification of the test specimen of FIG. 1.

As shown in FIGS. 2 and 3 a test specimen 6 according to the present invention comprises a generally cruciform, single piece of fiber-reinforced composite material. The piece of composite material comprises a first loading portion 10 lying in a plane P1, a second loading portion 20 lying in a plane P2 and a test gauge portion 30 that are integral. The first and second loading portions 10, 20 are in the form of elongate rectangular planar portions. The loading portions 10, 20 are planar and parallel to one another and are orientated perpendicular to one another such that they overlap at a mid-point. There is a portion of composite material located between the loading portions 10, 20 in the region of the mid-point and this is constitutes the test gauge portion 30. As shown in FIG. 4, the test gauge portion 30 has a square cross-section in a plane parallel to the loading portions 10, 20, that has dimensions equal to the width of the loading portions 10, 20. The transition between the loading portions 10, 20 and the test gauge portion 30 is filleted in order to reduce stress concentrations.

The first and second loading portions 10, 20 extend either side of the gauge portion 30 along first and second perpendicular axes A1, A2 respectively. This provides first and second loading surfaces 12, 14 on the first loading portion 10 and third and fourth loading surfaces 22, 24 on the second loading portion 20.

With reference to FIG. 5A the test specimen is manufactured from a small thin rectangular composite plate 40. As shown in FIG. 5B, two prismatic side pieces 42, are machined from the top surface of the plate 40, either side of the plate 40. These pieces 42, 44 are substantially rectangular and have a thickness that is less than that of the plate 40. This means that a second loading portion 20 is formed which extends either side of a central portion 46 (FIG. 5C). As shown in FIG. 5D, two prismatic side pieces 48, 50 are then machined from the lower surface of the plate 40, either side of the plate 40. These pieces 48, 50 are of a similar dimension to the prismatic side pieces 42, 44 but extend in a direction perpendicular to the prismatic side pieces 42, 44. As can be seen from FIG. 5E, the above steps result in the formation of a cruciform test specimen 6 as described above having first and second loading portions 10, 20 and a test gauge portion 30. Any suitable machining method can be used such as grinding using a silicon carbide wheel.

FIG. 6 shows an apparatus for testing the tensile strength of the composite test specimen 6. A lower U-shaped rig 60 and an upper U-shaped rig 66 are used to apply a tensile force to the test gauge portion 30 of the specimen 6. The lower U-shaped rig 60 applies an upwards force to the first loading portion 10 and the upper U-shaped rig 66 is used to apply a downwards force to the second loading portion 20. More specifically, the end faces 62, 64 of the lower rig 60 apply equal forces to the first and second loading surfaces 12, 14 of the first loading portion 10 and the end faces 68, 70 of the upper rig 66 apply equal forces to the loading surfaces 22, 24 of the second loading portion 20. These forces can be achieved by applying a compressive force between the upper and lower rigs 60, 66, which generates a tensile stress state in the test gauge portion 30.

FIG. 7 shows schematically an experimental assembly using the apparatus of FIG. 5. Steel balls 72, 74 are placed above and below the rigs 60, 66 and a compressive force is applied between them. The steel balls 72, 74 ensure that the force is applied perpendicular to the face of the upper and lower rigs 60, 66. The composite can then be tested to failure to determine the tensile strength of the composite.

FIG. 8 shows an embodiment in which steel beams (or plates) 76, 78 are adhesively bonded to the upper surface of the first loading portion 10 and to the lower surface of the second loading portion 20. This reduces the tendency of the loading portions 10, 20 to bend. When the specimen 6 is tested using the steel beams of this embodiment, the incidence of stress concentrations, in the region of the transition from the loading portions 10, 20 to the gauge portion 30, is reduced as compared to the above-described embodiment. The disadvantage of such bending and stress concentrations is that they can give rise to peeling in the loading portions of the test specimen, so that the test result will not accurately reflect the through-thickness properties of the test specimen.

When the test specimen 6 is loaded in the through-thickness direction in tension, it fails in the gauge section 30. The tensile force is transmitted into the gauge section 30 through the crossing of the loading portions 10, 20 without using an adhesive bond, therefore preserving the reinforcing effect of the through-thickness reinforcement.

This means that the test specimen 6 can be tested to tensile failure in the through-thickness direction, even if the composite is highly reinforced.

The test specimen 6 can also be produced with ease using the manufacturing technique described above. This requires only a small amount of composite material, so a large number of test specimens can be manufactured from a small amount of starting material.

Furthermore, because a compressive load is used to apply a tensile force to the gauge section 30, the test specimen 6 can be easily used with split. Hopkinson compression bars; this enables the characterisation of the through-thickness properties of the composite at high strain rates.

The invention claimed is:

1. A test specimen for testing the through-thickness tensile strength of a fiber-reinforced composite material, the test specimen comprising:
   a single piece of fiber-reinforced composite material including:
      a first loading portion having a first longitudinal axis in a first plane and a second loading portion having a second longitudinal axis in a second plane, the first and second planes being substantially parallel, the first and second axes being substantially perpendicular; and
      a test gauge portion formed by the first and second loading portions being configured to partially overlap, the test gauge portion being integral with the first and second loading portions, and the test gauge portion being configured to separate the first and second loading portions in a third direction perpendicular to both the first and second longitudinal axes, wherein:
      the first loading portion extends beyond the test gauge portion in opposite directions along the first axis to form first end regions and the second loading portion extends beyond the test gauge portion in opposite directions along the second axis to form second end regions, and
      in use, a first loading member applies a first force to the first end regions in the third direction, and simultaneously a second loading member applies a second force to the second end regions in a direction opposite to the third direction, so that a tensile force results in the test gauge portion.

2. The test specimen according to claim 1, wherein the fiber-reinforced composite material is a three-dimension reinforced composite material.

3. The test specimen according to claim 2, wherein the test specimen is of a generally cruciform shape.

4. The test specimen according to claim 1, wherein the transition between the first and second loading portions and the test gauge portion is filleted.

5. The test specimen according to claim 1, wherein a plate is attached to each of the first and second loading portions.

6. The test specimen according to claim 5, wherein the plates are metal.

7. The test specimen according to claim 5, wherein the plate is glued to the first and second loading portions.

8. A method of manufacturing the test specimen according to claim 1, comprising:
   machining first and second side portions from a first surface of a fiber-reinforced composite plate along a first axis; and
   machining third and fourth side portions off a second surface of the fiber-reinforced composite plate along a second axis that is oblique to the first axis, wherein the second surface is opposed to the first surface.

9. The method according to claim 8, wherein the first and second axes are perpendicular.

10. The method according to claim 8, wherein the first, second, third and fourth portions are prismatic.

11. The method according to claim 10, wherein the prismatic portions are substantially rectangular.

12. The method of testing the test specimen according to claim 1, comprising:
   applying a compressive force between the first loading portion and the second loading portion so as to transmit a tensile force to the test gauge section.

13. A test specimen for testing the through-thickness tensile strength of a fiber-reinforced composite material, the test specimen comprising:
   a single piece of fiber-reinforced composite material including:
      a first loading portion having a first longitudinal axis in a first plane and a second loading portion having a second longitudinal axis in a second plane, the first and second planes being substantially parallel, the first and second axes being substantially perpendicular; and
      a test gauge portion formed by the first and second loading portions being configured to partially overlap, the test gauge portion being integral with the first and second loading portions, and the test gauge portion being configured to separate the first and second loading portions in a third direction perpendicular to both the first and second longitudinal axes.

14. The test specimen according to claim 13, wherein the fiber-reinforced composite material is a three-dimension reinforced composite material.

15. The test specimen according to claim 13, wherein the test specimen is of a generally cruciform shape.

16. The test specimen according to claim 13, wherein the transition between the first and second loading portions and the test gauge portion is filleted.

17. The test specimen according to claim 13, wherein a plate is attached to each of the first and second loading portions.

18. The test specimen according to claim 17, wherein the plates are metal.

19. The test specimen according to claim 17, wherein the plate is glued to the first and second loading portions.

* * * * *